US00PP31449P2

(12) United States Plant Patent
Bourne

(10) Patent No.: US PP31,449 P2
(45) Date of Patent: Feb. 18, 2020

(54) GRAPEVINE NAMED 'SV30-7-115'

(50) Latin Name: *Vitis vinifera*
Varietal Denomination: SV30-7-115

(71) Applicant: Sunview Vineyards of California, Inc., Delano, CA (US)

(72) Inventor: Timothy F. Bourne, Visalia, CA (US)

(73) Assignee: Sunview Vineyards of California, Delano, CA (US)

( * ) Notice: Subject to any disclaimer, the term of this patent is extended or adjusted under 35 U.S.C. 154(b) by 0 days.

(21) Appl. No.: 16/350,142

(22) Filed: Oct. 2, 2018

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 5/0812
See application file for complete search history.

*Primary Examiner* — Kent L Bell
(74) *Attorney, Agent, or Firm* — Baker Manock & Jensen, PC; Eric C. Cole

(57) ABSTRACT

A new and distinct variety of grapevine plant named 'SV30-7-115' particularly characterized by its ovate to ellipsoidal shaped, green skinned berries which are very large, sweet and have crisp texture. Productivity is moderate, requiring cane pruning to achieve a full crop. Flower clusters of grapevine named 'SV30-7-115' respond well to gibberellic acid applications, producing well-filled clusters of large, ellipsoidal shaped berries.

2 Drawing Sheets

Latin name of the genus and species of the plant claimed: The plant claimed relates to a new and distinct variety of *Vitis vinifera.*

Variety denomination: The plant claimed shall be known as 'SV30-7-115'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV30-7-115'. As used herein, 'grapevine' refers to all plant parts including, vines, canes, tendrils, leaves, fruit and roots of 'SV30-7-115'. Grapevine named 'SV30-7-115' is the result of an effort to produce a high quality, green seedless grape with fruit characteristics superior to currently available cultivars. This new cultivar originated from a cross conducted in May 2009 near McFarland, Calif. between pistillate grapevine plant selection 'SV13-2-138' (unpatented) and the cultivar 'Princess' (unpatented). Resultant ovules from the cross were harvested 42 days after pollination and cultured on 'McCown's Woody Plant Medium' at a temperature of 22° C. for twelve weeks. Subsequently, the resultant embryonic plants were cultured in the same medium in the laboratory under twelve hours of light from standard fluorescent lamps at 26.4° C. The seedlings from this effort were transplanted to the greenhouse in October of 2009 and grown in the greenhouse at 26.4° C. with 12 hours' illumination under high pressure sodium vapor lamps. The seedling population of 404 plants was planted in the field in the spring of 2010 near Delano, Calif. The new grapevine was selected from this seedling population on Aug. 10, 2012. It was then propagated by cuttings and bench grafted to 'Freedom' (unpatented) rootstock in 2013. The present invention has been found to retain its distinctive characteristics through two successive asexual propagations.

Grapevine named 'SV30-7-115' differs from the female parent grapevine 'SV13-2-138' (unpatented) in that grapevine named 'SV30-7-115' has ovate to ellipsoidal shaped, green skinned, seedless berries and is self-fertile, whereas 'SV13-2-138' (unpatented) has spherical shaped, green skinned berries with partially lignified seed traces.

Grapevine named 'SV30-7-115' differs from its male parent 'Princess' (unpatented) in that grapevine named 'SV30-7-115' has green skinned berries while 'Princess' (unpatented) has oblong, yellow skinned berries. Additionally, clusters of grapevine named 'SV30-7-115' are generally larger than those of 'Princess' (unpatented) consistently setting full clusters while those of 'Princess' (unpatented) are smaller and less well-filled.

Grapevine named 'SV30-7-115' differs from the commercial cultivar 'SV21-66-226' (U.S. Plant Pat. No. 24,531) in that grapevine named 'SV30-7-115' has berries that are more elongate than those of 'SV21-66-226' (U.S. Plant Pat. No. 24,531). Additionally, berries on vines of grapevine named 'SV30-7-115' which have been sprayed with exogenous gibberellic acid are more elongate and cylindrical than those of 'SV21-66-226' (U.S. Plant Pat. No. 24,531) which are more ovate.

SUMMARY OF THE INVENTION

The following are the most outstanding and distinguishing characteristics of the ripe fruit of this new variety when grown under normal horticultural practices near McFarland, Calif. Some of the characteristics may vary depending upon changes in crop load and change of location of cultivation.

1. 1. Green skinned fruit;
2. Very firm berry texture; and
3. Very large, ovate to ellipsoidal shaped berries with sweet taste.

BRIEF DESCRIPTION OF THE DRAWINGS

Grapevine named 'SV30-13-10' is illustrated by the accompanying photographs which show fruit clusters, leaves, canes, and tendrils. The colors shown are as true as can be reasonably obtained by conventional photographic procedures.

DETAILED BOTANICAL DESCRIPTION

Figure 1:
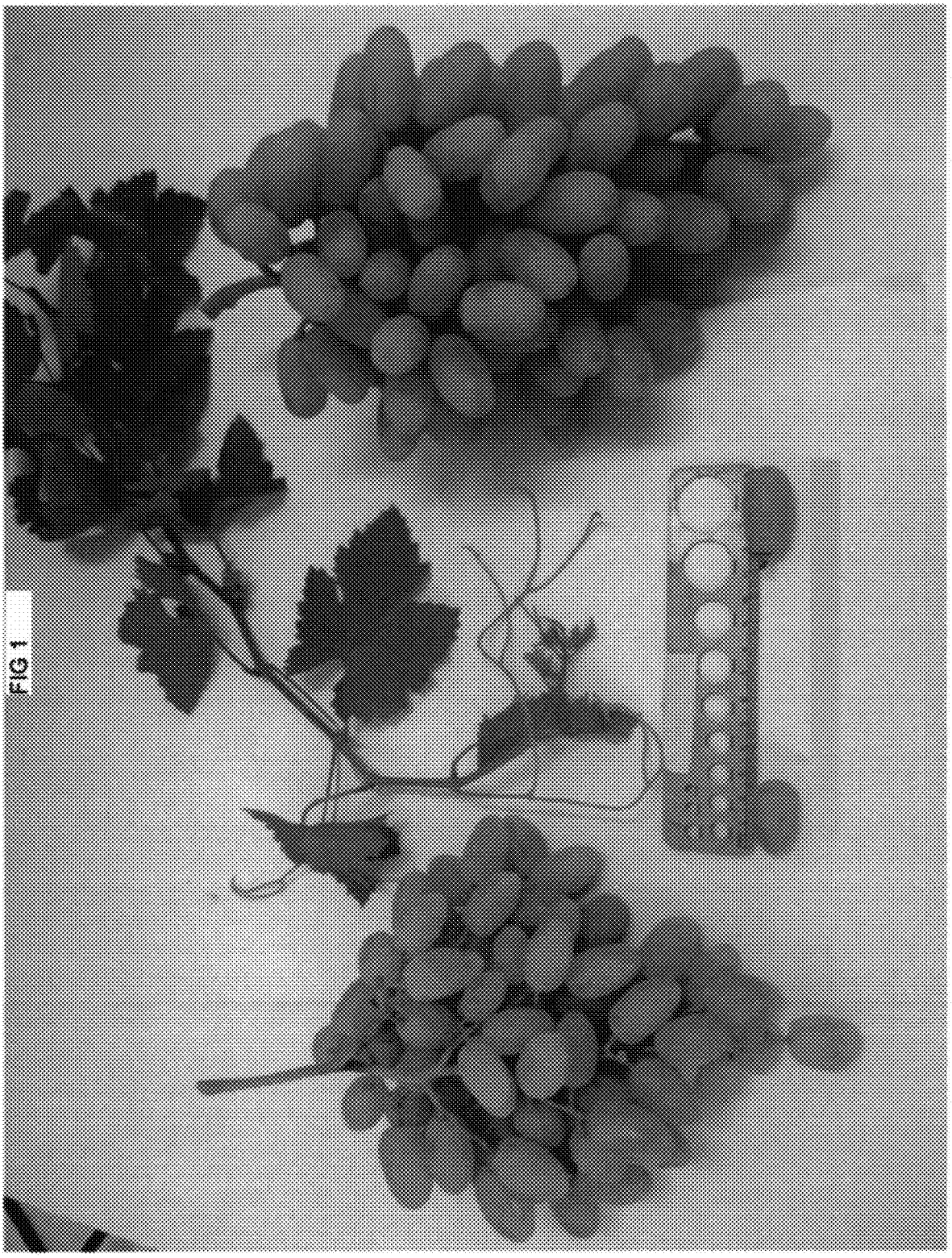
FIG. 1 Natural fruit cluster and cluster sprayed with gibberellic acid with shoots, leaves, tendrils and shoot tips from 5 year old plants grown near McFarland, Calif. in 2018.
Figure 2:
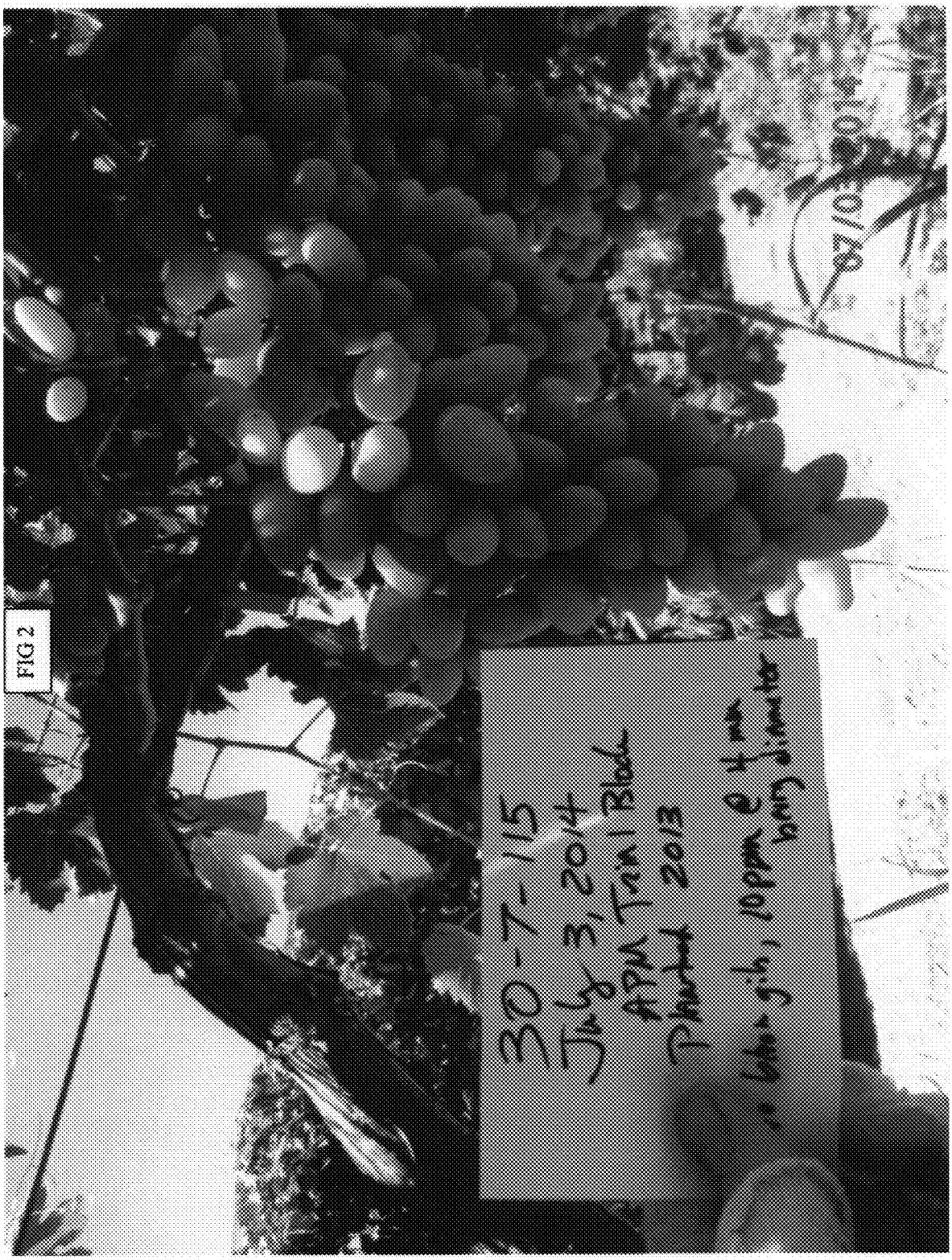
FIG. 2 Fruit clusters on vine sprayed with gibberellic acid and trunk girdled from 1 year old plants grown near McFarland, Calif. in 2014.

The following detailed description sets forth the distinctive characteristics of grapevine named 'SV30-7-115'. Descriptions of the new invention apply to vines of grapevine named 'SV30-7-115' grown on 'Freedom' (unpatented) rootstock at a density of 1,537 vines per hectare grown near McFarland, Calif. in 2018. These vines were in their fourth year of full production, having been planted in 2013. These descriptions are believed to apply generally to the new variety grown under similar circumstances elsewhere. References to color correspond to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis* spp.) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV30-7-115'.

Plant:

*Vigor*.—Medium; vines spur-pruned and shoot thinned to 32 shoots, averaging 232 cm. of growth per cane.
*Density of foliage*.—Moderate.
*Productivity*.—Very productive when cane pruned, up to 32,000 kg/hectare.
*Hardiness*.—Hardiness observed to 0° C.
*Rootstock*.—'Freedom' (unpatented).

Trunk:

*Shape*.—Broadly elliptical.
*Straps*.—Long, split.
*Surface texture*.—Shaggy.
*Inner bark color*.—RHS Greyed Orange group 174B.
*Outer bark color*.—RHS Brown group N200B.

Growing tips (young shoot):

*Pubescence*.—Sparse, prostrate.
*Color*.—RHS Yellow Green Group 144B.
*Anthocyanins*.—Absent.
*Shape*.—Flattened.
*Apex*.—Open.
*Shoot attitude*.—Erect.

Young leaves and shoots:

*Immature leaf color*.—Upper surface: RHS Yellow Green group 144A. Lower leaf surface: RHS Yellow Green group 143A.
*Young shoot internode color* (*in full sun, upper surface*).—Red Purple group 61A and Yellow Green group 144B.
*Young shoot internode color, upper surface* (*in shade*).—Yellow green group 144B.
*Young shoot internode color, lower surface* (*in shade*).—Yellow green group 144C.
*Young shoot node color, upper surface* (*in shade*).—Yellow green group 144A.
*Young shoot internode color, lower surface* (*in shade*).—Yellow green group 144B.
*Erect hairs on internodes*.—Absent.
*Erect hair on nodes*.—Absent.

Lateral shoots:

*Shape*.—Elliptical.
*Number*.—Variable from shoot to shoot, occurring on some shoots at node 7 and above. Some shoots with no laterals.
*Length*.—14.3 cm.
*Diameter*.—5 mm.
*Internode length*.—2 cm.
*Color*.—Yellow green group 144D.

Mature leaves:

*Average blade length*.—14.3 cm.
*Average blade width*.—17.7 cm.
*Size of blade*.—Large.
*Shape*.—Pentagonal.
*Anthocyanin coloration of main veins on the upper side of the blade*.—Slight; restricted to bases of main veins on sun exposed leaves: RHS red purple group 60B.
*Mature leaf profile*.—Mostly flattened; some leaves with undulation of the margins.
*Blistering* (*upper surface*).—Absent.
*Leaf blade tip*.—In plane of blade.
*Margins*.—Lobed, serrated, undulating.
*Apex*.—Broadly acute.
*Bases*.—Sagittate.
*Thickness*.—Medium.
*Undulation of blade between main and lateral veins*.—Slight.
*Shape of teeth*.—Broadly conical, both sides convex.
*Length of teeth*.—3-10 mm.
*Ratio length/width of teeth*.—About 1:1, slightly wider than long.
*General shape of petiole sinus*.—Wide open.
*Tooth at petiole sinus*.—Absent.
*Petiole sinus limited by veins*.—Absent.
*Shape of upper lateral sinus*.—Closed.
*Prostrate hairs between veins* (*lower surface*).—Absent.
*Erect hairs between veins* (*lower surface*).—Absent.
*Prostrate hairs on main veins* (*lower surface*).—Very sparse.
*Density of erect hairs on main veins* (*lower surface*).—Sparse; limited to junctions of main veins.

*Prostrate hairs on main veins* (*upper surface*).—Sparse.

*Upper surface*.—Summer color: RHS Green group 139A. Surface texture: Smooth. Surface appearance: Dull. Goffering of blade: Absent.

*Lower surface*.—Summer color: RHS Green group 137A. Anthocyanin coloration of main veins on lower leaf surface: Slight; limited to bases of main veins on sun exposed leaves: RHS red purple group 60B. Anthocyanin coloration on laterals: No. Glossiness: Low. Pubescence: Absent. Surface texture: Smooth. Surface appearance: Dull.

*Petiole*.—Length: 13.2 cm. Diameter: 4 mm. Length of petiole compared to middle vein: Slightly shorter. Density of prostrate hairs: Absent. Density of erect hairs: Absent. Color: In shade: RHS Green group 143C. In sun: RHS Red Purple group 59C.

Tendrils:

*Number*.—Tendrils occurring on 50% of shoots at the 7th node of main shoot. Tendril formation on strong lateral shoots beginning on node 7 and on most nodes above that node.

*Color*.—In shade: RHS Yellow green group 144B. In sun: The proximal one half: RHS Red Purple group 59B. The distal one half: RHS Yellow Green group 144B.

Flowers:

*Flower sex*.—Perfect.

*Position of first flowering nodes*.—Usually on node 4.

*Number of inflorescences per shoot*.—On spur pruned vines, one cluster on one half of shoots; other shoots sterile. Date of full bloom: May 11th.

*Flower cluster shape*.—Pyramidal.

*Flower cluster length*.—20.4 cm.

*Flower cluster width*.—7 cm.

*Color of flower cluster stems*.—RHS yellow green group 144B.

*Calyptra color*.—RHS green group 143C.

*Ovary color*.—RHS green group 134A.

*Ovary length*.—3 mm.

*Ovary width*.—1.5 mm.

*Filament length*.—2 mm.

*Filament color*.—Translucent, absence of color.

*Anther length*.—1 mm.

*Anther color*.—RHS yellow group 154C.

Fruit:

*Berry firmness*.—Firm.

*Bloom* (*cuticular wax*).—Very waxy.

*Adherence of berries*.—Moderate; removal from pedicel with some difficulty.

*Skin thickness*.—Thin, not noticeable when chewing.

*Reticulation*.—Absent, skin surface is smooth and uniform.

*Tenacity*.—Flesh adheres to skin tenaciously.

*Ripening period*.—Mid-season.

*Date of ripening*.—August 2nd at McFarland, Calif.

*Particular flavor*.—Neutral *Vitis vinifera*.

*Use*.—Fresh market.

*Keeping quality*.—Good.

*Shipping quality*.—Good.

*Date of first harvest*.—August 2nd.

*Solids-sugar*.—22 brix at full maturity.

*Refractometer test*.—22.0 brix.

*Cluster*.—Bunch Size: Large. Length (peduncle excluded): 27.1 cm. Width: 16.3 cm. Weight: Natural, without gibberellic acid treatment: 1.0 kg. Weight: Cluster from vine treated with gibberellic acid and tipped to 19 cm length: 665 g. Density: Well-filled. Number of berries natural cluster: 144. Number of berries on clusters treated with gibberellic acid and tipped to 19 cm length: 64. Form: Long, conical with occasional shoulder.

*Peduncle*.—Diameter: 7 mm. Length: 5.0 cm. Lignification: Slight, 1 cm of lignification at ripening. Color: RHS Yellow green group 144B.

*Berry*.—Size: Large. Uniformity of size: Uniform. Weight Natural, without gibberellic acid treatment: About 6.3 g. Treated with gibberellic acid on tipped cluster: 10.5 g. Shape: Ovate to ellipsoidal. Presence of seeds: Seedless; most berries develop one or two ovule traces about 2 mm in length. Cross section: Circular. Dimensions: Longitudinal axis: About 3.0 cm. Horizontal axis: About 2.0 cm. Skin color (without bloom): RHS Yellow Green group 145B. Flesh color: Translucent, RHS yellow green group 144D. Juiciness of flesh: Very juicy. Berry firmness: Very firm. Particular flavor: Neutral, typical *vinifera*. Bloom (cuticular wax): Heavy. Pedicel color: Yellow green group 144C. Pedicel length: About 6-10 mm. Pedicel diameter: 2 mm. Berry separation from pedicel: Difficult.

*Skin*.—Thickness: Thin, not noticeable when chewing. Texture: Crisp. Reticulation: Absent, skin surface is smooth and uniform. Roughness: Absent. Tenacity: Tenacious to flesh. Tendency to crack: Resistant.

Mature canes:

*Cane color*.—RHS Greyed Orange group 166C.

*Surface texture*.—Smooth.

*Shape*.—Broadly elliptical.

*Internode length*.—13.1 cm.

*Color mature cane internode upper surface*.—Greyed orange group 166A.

*Color mature cane internode lower surface*.—Greyed orange group 166C.

*Color mature cane node upper surface*.—Greyed orange group 175A.

*Color mature cane node lower surface*.—Greyed orang group 175C.

*Dormant bud color*.—RHS Greyed Orange group 165A.

Disease and insect resistance: Moderately susceptible to powdery mildew which may be controlled with standard fungicides in Calif.

Having thus described and illustrated our new variety of grapevine, I claim:

1. A new and distinct variety of grapevine plant named 'SV30-7-115' substantially as illustrated and described herein.

* * * * *